United States Patent [19]

Warrington et al.

[11] Patent Number: 4,940,659
[45] Date of Patent: Jul. 10, 1990

[54] SCREENING EXTRA-CELLULAR BODY FLUIDS FOR SUPEROXIDE DISMUTASE (SOD-1) FOR DETERMINING FETAL TRISOMY 21 DOWN SYNDROME

[75] Inventors: Richard E. Warrington; Abbas A. Khan, both of Houston, Tex.; Carl R. Merril, Rockville, Md.

[73] Assignee: Monoclonetics International, Inc., Houston, Tex.

[21] Appl. No.: 17,152

[22] Filed: Feb. 20, 1987

[51] Int. Cl.$^5$ .................. G01N 33/53; C12Q 1/44; C12Q 1/26
[52] U.S. Cl. .......................... 435/7; 435/19; 435/25; 436/548; 436/811
[58] Field of Search ............. 435/7, 19, 25, 68, 172.2, 435/240.2; 436/548, 811

[56] References Cited

U.S. PATENT DOCUMENTS

| 4,340,675 | 7/1982 | Johansen | 435/189 |
|---|---|---|---|
| 4,341,867 | 7/1982 | Johansen | 435/189 |
| 4,346,174 | 8/1982 | Yasuda | 435/189 |
| 4,351,899 | 9/1982 | Owen | 435/26 |
| 4,376,110 | 3/1983 | David et al. | 436/513 |
| 4,388,406 | 6/1983 | Johansen | 435/189 |
| 4,390,628 | 6/1983 | Johansen | 435/189 |
| 4,394,449 | 7/1983 | Modrovich | 435/188 |
| 4,435,506 | 3/1984 | Jackson et al. | 435/189 |

FOREIGN PATENT DOCUMENTS

| 193204A | 3/1986 | European Pat. Off. | 435/25 |
|---|---|---|---|
| 2017542 | 8/1987 | European Pat. Off. | 435/25 |
| 2089979 | 3/1982 | United Kingdom | 435/25 |
| 2089980 | 6/1982 | United Kingdom | 435/25 |

OTHER PUBLICATIONS

Patent Abstracts of Japan, vol. 9, No. 254 (C-308), Oct. 11, 1985 and Japan Patent 60-109528(A) Fujisawa Yakuhin et al.
Clinical Genetics, vol. 33, No. 1, Jan. 1988, pp. 11-19, Munksgaard International Publishers, Copenhagen, DK, A, Jeziorowska et al.: "Regular Trisomy 21 Not Accompanied by Increased Copper-Zinc Superoxide Dismutase (SOD1)activity".
Human Genetics, vol. 75, No. 3, 1987, pp. 251-257, Springer Verlag, Heidelberg, DE; J. L. Huret et al.: "Down Syndrome with Duplication of a Region of Chromosome 21 Containing the CuZn Superoxide Dismutase Gene Without Detectable Karyotypic Abnormality".
Patent Abstracts of Japan, vol. 7, No. 78 (P-188), Mar. 31, 1983 and Japan Appl. No. 58-7560 (A), Filed 1/17/83, Mamoru Sugiura.
Baeteman, M. A. et al., "Immunoreactive SOD-1 in Amniotic Fluid, Amniotic Cells and Fibroblasts from Trisomy 21 Fetus", Acta Paediatr Scand, vol. 74, pp. 697-700, 1985.
Derwent Abstract of JP 60-262597.
Derwent Abstract of JP 61-1025497.
Derwent Abstract of DT 3236388.
Derwent Abstract of DT 3410159.
Derwent Abstract of JP 60 0012999.
Chemical Abstract 97:87493.
Chemical Abstract 103:176901.

(List continued on next page.)

Primary Examiner—Esther M. Kepplinger
Assistant Examiner—Carol A. Spiegel
Attorney, Agent, or Firm—David A. Rose; Ned L. Conley

[57] ABSTRACT

Disclosed is a screening assay for determining the amount of Superoxide Dismutase (SOD-1) in extra-cellular body fluids, for use in determining Trisomy 21 Down syndrome in a fetus. The assay can be done by any of a number of well known techniques including Radioimmunoassay, an Enzyme Linked Immunoassay, or a luminescence assay, single or tandem antibody type, carried out in solid or liquid phase. Polyclonal or monoclonal antibodies can be used. In the preferred embodiment, the assay is used to determine SOD-1 levels in amniotic fluid. A level above a threshold indicates a high probability of Trisomy 21 Down Syndrome for the fetus.

4 Claims, 2 Drawing Sheets

OTHER PUBLICATIONS

Biological Abstract 81:1000970.

Biological Abstract 81:21516.

Baret et al., "A Radioimmunoassay for Copper Containing Superoxide Dismutase", Biochemical and Biophysical Research Communications, vol. 88, No. 2, (1979), pp. 337–345.

Del Villano et al., "A Radioimmune Assay for Human Cupro-Zinc Superoxide Dismutase and Its Application to Erythrocytes", Journal of Immunological Methods, vol. 29, (1979), pp.253–262.

Groner et al., "The Human CuIZn Superoxide Dismutase Gene Family: Architecture and Expression of the Chromosome 21-Encoded Functional Gene and Its Related Processed Pseudogenes" in Rotilio, Superoxide and Superoxide Dismutase in Chemistry, Biology and Medicine (Elsevier Science Publishers, 1986), pp. 257–265.

Porstmann et al., "A Rapid and Sensitive Enzyme Immunoassay for CuIZn Superoxide Dismutase With Polyclonal and Monoclonal antibodies", CLINICA CHIMICA ACTA, vol. 171 (1988) pp. 1–10.

Tietz, N (ed.), Textbook of Clincal Chemistry, (W. B. Saunders Company, 1986), pp. 663–667.

Derwent Abstract of –JP–105075 (17.01.83).

Derwent Abstract of JP 053485 (20.09.86).

SCREENING EXTRA-CELLULAR BODY FLUIDS FOR SUPEROXIDE DISMUTASE (SOD-1) FOR DETERMINING FETAL TRISOMY 21 DOWN SYNDROME

FIELD OF THE INVENTION

The invention relates to the detection of potential Down syndrome progeny (Trisomy 21) by screening for the presence of SOD-1 in extra-cellular body fluid.

BACKGROUND OF THE INVENTION

Trisomy 21 (i.e., one additional 21st chromosome) accounts for 95 per cent of all cases of Down syndrome. This condition is among the most common genetic defects, occurring in about 1 in every 800 births. Patients with this syndrome have characteristic faces, are mentally retarded, and at least 30 per cent have congenital heart disease.

Trisomy 21 occurs when homologous chromosomes fail to separate at anaphase, resulting in nondisjunction and the production of one monosomic and one trisomic daughter nuclei. In chromosomally normal women, the frequency of nondisjunction is age related. For women ages 20 to 30, the incidence increases linearly from about 0.3 per 1000 births to about 2 per 1000 births. After the age of 30, the incidence increases exponentially, at a rate of about 30 per cent per year. Women over 35 give birth to 35 per cent of all children with Trisomy 21 Down Syndrome.

Women under 20 also show an increasing incidence of Trisomy 21 Down syndrome with falling age. Thus, a woman age 15 has about the same chance of having a Down syndrome child as a woman between the ages of 30 and 35.

The risk for a woman under the age of 30 of having a second child with Trisomy 21 Down syndrome is 1.4 per cent. Her risk after the age of 30 is 1 per cent plus the risk factor for a woman of that age.

The nondisjunction which results in Trisomy 21 Down syndrome can also occur in the male. Nondisjunction in the male accounts for 20 to 25% of children with this syndrome. For fathers over the age of 55, the risk of having a Down syndrome child may be about twice that expected after adjustment for the mother's age.

Prior to birth, a fetus with genetic defects (including Trisomy 21) can be detected through amniocentesis. In amniocentesis 10 to 20 ml of amniotic fluid are withdrawn from the amniotic cavity between the 15th and 16th week of pregnancy. The amniotic fluid cells are then cultured in tissue culture for about two weeks. The cells are stained, and the chromosomes are counted to identify genetic abnormalities such as Trisomy 21.

Cell culturing is, however, an expensive, skilled laborintensive, and time-consuming process, often costing up to $1200. Further, the cultures are easily destroyed if contamination enters. Thus, prior to cell culturing, the fluid is often screened for proteins which indicate the existence of certain defects (so-called "genetic markers.") If the screening is positive, cell culturing can then be done to verify the existence of the defect. If negative, the expense of culturing can be foregone. Screening is currently commonplace, because many pregnant women are now being advised to have amniotic fluid withdrawn and screened for the genetic marker Alpha Fetoprotein ("AFP").

Elevated levels of AFP indicate open neural tube defects, such as anencephaly and Spina Bifida, as well as other fetal abnormalities. Although some women carrying a Trisomy 21 fetus will show abnormal AFP levels, many will show no deviation from normal limits.

Thus, the current screening tests for Trisomy 21 are deficient. Further, because of the expense of the more accurate cell culturing technique, this test is often foregone by the patient. In view of the frequency with which Trisomy 21 occurs, a marker (and a screening test based on such marker) which gave a truer indication of the presence of Trisomy 21 would clearly be desirable, particularly for women in the higher risk groups.

By 1981 it was recognized that Trisomy 21 patients showed increased levels of SOD-1 in Red Blood Cell lysates. See B. C. Del Villano & J. A. Tischfield, "Quantitation of Human Cuprozinc SOD-1 by Radioimmunoassay and Its Possible Significance in Disease," *Immunoassay Methods* at 366–67 (1981). However, there is no suggestion in this article to screen body fluid for SOD-1 as a test for Trisomy 21. The authors only state that this discovery could shed light on the role of SOD-1 in normal metabolism, or indicate the consequences of having excess SOD-1. They also indicate that further experiments could relate the SOD-1 level to the degree of retardation.

A 1985 study sought to determine whether increased levels of SOD-1 were to be found in Trisomy 21 fetal fibroblasts, amniotic cells and amniotic fluid. See M. A. Bateman, M. G. Mattei, A. Abret, M. Gamerre & J. F. Mattei, "Immunoreactive SOD-1 in Amniotic Fluid, Amniotic Cells and Fibroblasts from Trisomy 21 Fetus," *Acta Poediatr. Scand.* 74:697–700 (1985). The authors concluded that it was not possible to establish a relationship between SOD-1 levels in amniotic fluid and Trisomy 21 in the fetus. Id. at 699. Thus, if increased SOD-1 levels in amniotic fluid (or other body fluids of the mother) correlated with a Trisomy 21 fetus, this would be a significant departure from the teachings of the prior art.

SUMMARY OF THE INVENTION

The invention relates to the detection of increased levels of SOD-1 in amniotic fluid, as a screening test for Trisomy 21 Down's syndrome in the fetus. It has been discovered that increased levels of SOD-1 occur in the extra-cellular body fluid, in particular in amniotic fluid with a Trisomy 21 fetus. Increased levels of SOD-1 are believed to also occur in blood, sera, and other extra-cellular body fluids of the mother carrying a Trisomy 21 fetus. Thus, the screening test could also be used for measuring SOD-1 levels in any such fluids.

The detection can be done with either a monoclonal or polyclonal antibody, using any standard assay technique. For example, the following can be used: an Enzyme Linked Immunoassay, a Radioimmunoassay ("RIA"), a luminescence assay, all of which can be single antibody type or a double monoclonal antibody immunometric assay and all of which can be carried out in solid or liquid phase.

This screening test is relatively quick and simple to perform. If this screening test shows that the SOD-1 levels in the fluid are above the threshold, a cell culture can then be done to confirm the result.

It appears that this screening test can be performed relatively early in the pregnancy; perhaps as early as the twelfth week. The SOD-1 levels in extra-cellular body fluids are believed to show a sufficient increase at that time.

Another possible use of an assay for SOD-1 would be in detection of Alzheimer's disease. This condition is known to be associated with chromosome 21.

MANNER AND PROCESS OF MAKING AND USING THE INVENTION

Figure 1:
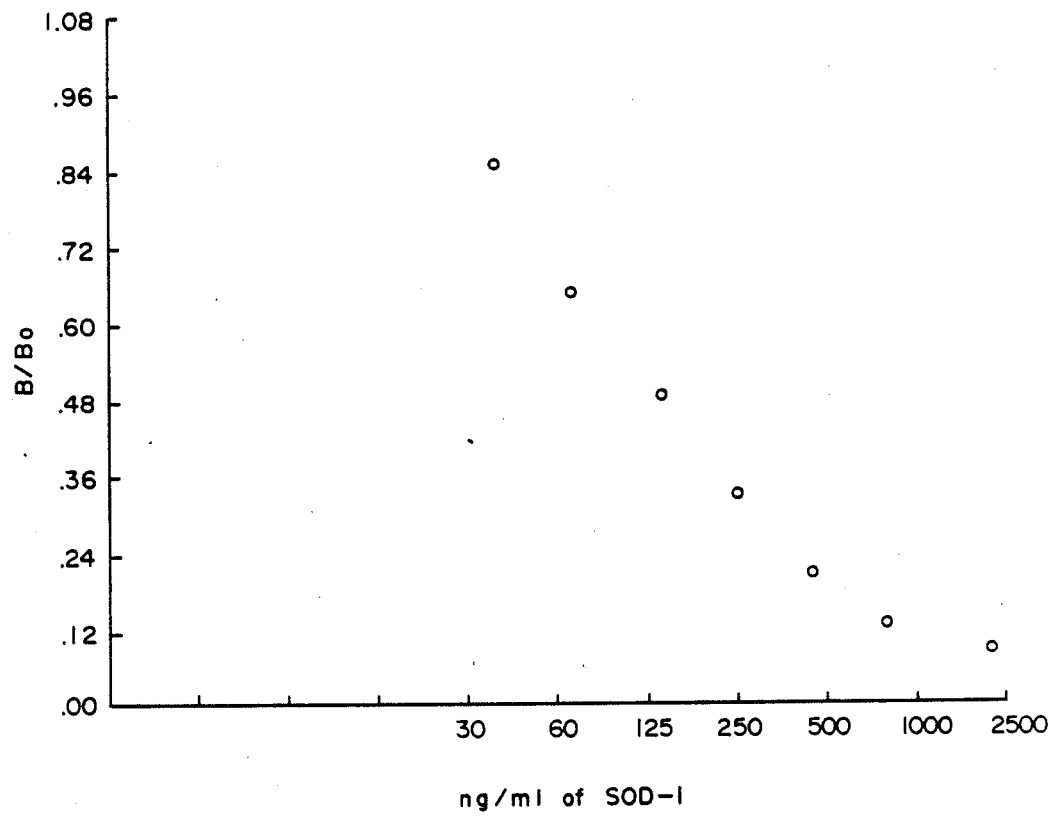
FIG. 1 is a graph showing B/Bo versus the concentration of Cu-Zn Superoxide Dismutase (SOD-1) in several samples.

Making and Selecting The Monoclonal Antibody (i) Immunization: 8 Balb/c mice which were 4 to 6 weeks old were selected for immunization. SOD-1 was diluted in normal saline (0.9%) and then emulsified in Freund's complete adjuvant by drawing it in and out of a syringe. The final solution contained 100 to 200 ug of SOD-1 per 100 ul, and 100 ul was injected intradermally into different sites in each mouse. A booster injection of the same amount of SOD-1 at the same concentration was given after 4 to 6 weeks. This time, however, the SOD-1 was emulsified in incomplete Freund's adjuvant.

4-6 weeks after the booster was given, the mice were again immunized with the same amount and concentration of SOD-1 (mixed in normal saline) by intrasplenic injection. Four days later, the mice were sacrificed and their spleens were removed in preparation for the fusion.

(ii) Fusion for Hybridoma: From the spleens, single cell suspensions of spleen cells were prepared. Spleen tissue was diluted in Dulbeccos Modification of Eagles Basal Medium (DMEM) and spun in a centrifuge at 1000 g for 10 minutes. The supernatant was withdrawn, and sp2/o myeloma cells maintained in culture were added to the cell pellet and resuspended.

The resultant suspension was then spun at 1000 g for 10 minutes, and the supernatant was withdrawn. 2 ml of polyethylene glycol 4000 was then added gradually over 10 minutes, together with 20 ml of DMEM.

The fused cells were spun down, the supernatant was withdrawn, and the cells were resuspended in 100 ml of DMEM and added in aliquots of 100 ul to each of 96 wells of a 96 well plate. 10 plates were so prepared. The fusion products were grown in the plates for two weeks. See also K. Flurkey, M. B. Bolger & D. S. Linthicum, "Preparation and Characteristics of Antisera and Monoclonal Antibodies to Serotonergic and Dopaminergic Ligands," 8 *J. Neuroimmunol.* at 115-127 (1985) for a description of a hybridoma production procedure.

(iii) Screening Process: The screening process was to pick up the SOD-1 antibody producing clones in the wells. 100 ul of the hybridoma supernatant (some of which should contain the SOD-1 antibody) was transferred to 96 well polyvinyl chloride plates. The plates had previously coated with goat anti mouse IgG (which can be purchased from Miles Laboratories) at a concentration of 0.05 mg/ml. The plates were then incubated for 2 hours at 37° C. After washing the plates, $^{125}$I labeled SOD-1 (labeled as described by Villano & Tischfield supra at 363) was added. The labeled SOD-1 was diluted in borate buffer saline, 0.1% BSA until it displayed roughly 5000 counts per minute ("CPM") per 100 ul.

After incubating for 2 hours at 37° C., the plates were washed twice and the wells were cut off with a hot michrome wire and transferred into plastic tubes for gamma spectroscopy.

The samples corresponding to the wells showing the highest CPM, and therefore the most antibody producing cells were then limit diluted and re-screened to assure the presence of only one clone. The cells were then grown in larger plates.

After growing, 1-3 million of the cells were injected into the peritoneal cavities of a mouse which had been primed 1 week before with pristane. Fluid from the peritoneal cavity was withdrawn 8-10 days later, and the ascites fluid was collected. Different titres of the ascites fluid were made by dilution with borate buffer saline pH 8.2-8.4 with 0.1% BSA. Those titres which exhibited 30-50% binding of SOD-1 (as determined by the RIA technique described below) were then selected for further evaluation by a RIA screening procedure.

The RIA screening procedure was to characterize the antibodies in terms of their specificity, sensitivity, and affinity for SOD-1. 100 ul of the selected titres together with 100 ul of various concentrations of SOD-1 and 100 ul of $^{125}$I SOD-1 displaying 25,000 CPM, was added into polyethylene tubes and incubated for 4 hours at room temperature. Goat anti mouse IgG, diluted 1:1, was then added with polyethylene glycol 6000, and incubated for 15 minutes after vortexing the tubes. The tubes were spun for 15 minutes at 2500 g. The supernatant was decanted and the pellet was assessed for radioactivity.

This final screen was to determine whether 30 ng/ml of unlabeled SOD-1 caused significant displacement of labeled SOD-1 from the antibody binding sites in a reasonable time (4 hours was considered optimal). In other words, this step was to select those monoclonal antibodies which had a greater sensitivity for the unlabelled antibody than for the labeled. To achieve this, the final CPMs in the pellets were compared with the counts in reference pellets. The reference pellets were produced by precipitation of goat anti mouse IgG, antibody and $^{125}$I SOD-1 as described above, with the only difference being that no unlabelled SOD-1 was present. Only those samples of antibody which showed a significant reduction in CPM over the reference (and thus significant binding of unlabelled SOD-1) would be selected for use in determining SOD-1 levels in amniotic fluid. See also K. F. Miller, D. J. Bolt & R. A. Goldsby, "A Rapid Solution-Phase Screening Technique for Hybridoma Culture Supernatants Using Radiolabelled Antigen and a Solid-Phase Immunoadsorbent," 59 *J. Immunol. Methods* at 277-280 (1983) for description of an RIA screening process.

It turned out that no monoclonal antibodies of sufficiently high affinity were obtained. Nevertheless, it must be emphasized that the monoclonal antibodies which were obtained would function adequately for determining SOD-1 levels in amniotic fluid. The reason that they were not so used was that polyclonals with a higher affinity for unlabelled SOD-1 were obtained by the process described below.

Making and Selecting the Polyclonal Antibodies (i) Immunization: 8 Balb/c mice were immunized by essentially the same procedure as that described for the monoclonal. The only difference was that no final intrasplenic injection was given.

10-12 days after the booster injection was given, the blood was withdrawn, spun down, and the serum collected from each mouse. This serum, containing the polyclonal antibodies, was then screened essentially by the same RIA screening process described above.

(ii) RIA screening: Several different titres of sera from each mouse were made by diluting the sera with borate buffer saline pH 8.2-8.4, 0.1% BSA. The titres which exhibited 30-50% binding of SOD-1 (as determined by the RIA technique) were then selected. A 1:1000 titre of sera from 2 of the 8 mice was chosen.

These titres were then checked to determine whether 30 ng/ml of unlabeled SOD-1 caused significant displacement of labeled SOD-1 from the antibody binding sites within a four hour period. The results were satisfactory, and these titres were deemed acceptable for use in determining SOD-1 concentrations in amniotic fluid.

Because more sera is required for polyclonals than for monoclonals, a larger animal than a mouse is needed to produce polyclonals in commercial quantities. The same polyclonal immunization and selection procedure described above can also be carried out in larger animals, for example goats.

Example of Using the Polyclonals in a Radioimmunoassay

Determination of SOD-1 levels in amniotic fluid was done with the 1:1000 polyclonal titre selected, and using an RIA. However, the polyclonals (or the monoclonals) could be used to determine SOD-1 levels with any of a number of techniques, including enzyme linked immunoassay and luminescence assay, single antibody type or a double monoclonal antibody immunometric assay, as carried out in solid or liquid phase. See Vol. 74, *Methods in Enzymology* part C for general description of a luminescence assay; T. E. Koerdte, J. E. Butler, 83 *Journal of Immunological Methods* at 283-299 (1985) for general description of a solid phase RIA and solid phase enzyme linked immunoassay; U.S. Pat. No. 4,376,110 for general description of a tandem type assay. In addition, any of these techniques could be used to determine SOD-1 levels in blood, sera or other body fluids, for detecting a Trisomy 21 fetus.

The RIA was done essentially as described above for the RIA screening procedure. This time, however, several various known concentrations of SOD-1 were mixed with the 1:1000 polyclonal titre and the labeled SOD-1. After the goat anti mouse IgG was added, the pellet was assessed for radioactivity. From using the samples with known concentrations of SOD-1, a standard curve was developed to be used in determining SOD-1 concentrations in unknown fluid samples. The procedure is described in greater detail below.

(i) Checking Procedure

The system must be checked to ensure proper binding. Labeled SOD-1 was added to a tube and the adjusted mean CPM was calculated.* (Hereinafter "Total"). Into another tube, SOD-1, antibody and goat anti mouse IgG were then added, and the adjusted mean CPM of the pellet was calculated. (Hereinafter "$B_0$"). The $B_0$/Total $\times$ 100 should be 35% plus or minus 3%. It was found to be 34.8%.

The system is also checked to ensure that non-specific binding counts are within normal limits. An assay is run with all unlabelled SOD-1 and the adjusted mean CPM of the pellet is calculated. This value is designated "Blank." "Blank"/Total $\times$ 100 should be less than 10%. It was found to be 6.8%.

An RIA with seven standards containing known concentrations of SOD-1, ranging from 30 ng/ml to 2500 ng/ml, was then conducted. The adjusted mean CPM of the seven pellets was calculated (hereinafter "B"), and $B/B_0$ was plotted against the concentration of each sample to yield the standard curve shown in FIG. 1.

Figure 2:
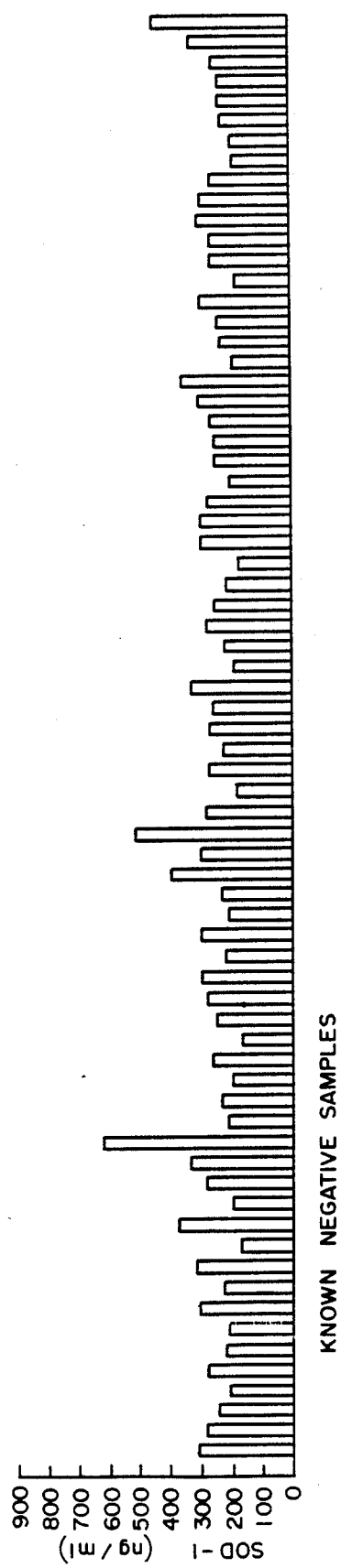
FIG. 2 is a graph showing the concentration of Cu-Zn Superoxide Dismutase (SOD-1) in 71 different samples known to be negative for Trisomy 21.
Figure 3:
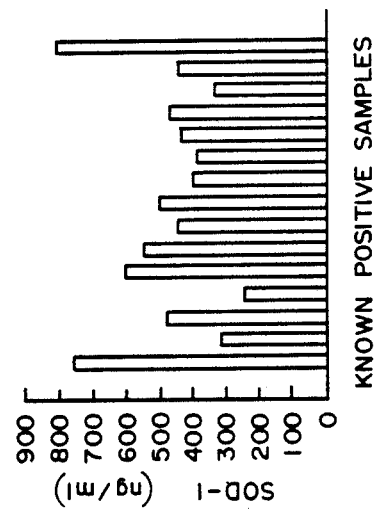
FIG. 3 is a graph showing the concentration of Cu-Zn Superoxide Dismutase (SOD-1) in 15 different samples known to be positive for Trisomy 21.

The RIA was then done with 71 different samples of amniotic fluid in which the fetus was known to be negative for Trisomy 21, and with 15 known positive samples, all of which were diluted 1:1. The standard curve was used to correlate the $B/B_0$ values obtained and determine the nanograms per ml of SOD-1 in the amniotic fluid. The results appear in bar graph form shown in FIGS. 2 and 3.

Of the 71 known negative samples, only 9 (or 13%) showed SOD-1 levels above 314 ng/ml.** Thus, 87% of the known negatives were below the threshold. Of the 15 known positive samples, only 1 (or 7%) showed SOD-1 levels below 314 ng/ml. Thus, 93% of the known positives were above the threshold level. Further analysis of the samples studied and/or a statistical analysis of data will likely provide explanation for (or compensation for) these slight aberrations. Nevertheless, these results show that the assay is suitable as a screening test for determining which patients should undergo cell culturing.

** This 314 ng/ml value was selected as a threshold level for indication of Trisomy 21 in amniotic fluid.

It should be understood that the description and examples above are exemplary only and not limiting, and that the scope of protection is defined in the claims which follow, and includes all equivalents of the subject matter of the claims.

What is claimed is:

1. A method for detecting a likelihood of Trisomy 21 Down's Syndrome in a fetus comprising:

assaying to determine the concentration of cuprozinc superoxide dismutase (SOD-1) in an extra-cellular body fluid of a mother in at least the twelfth week of pregnancy;

assaying samples of control maternal extra-cellular body fluid of the same type and substantially the same gestational age as the body fluid specimen from the mother, some of said samples being known to be positive and some negative for fetal Trisomy 21 Down's syndrome, to determine a threshold minimum concentration of SOD-1, which is the concentration at which the number of false positive or false negative samples is minimized, or the number of false positive and false negative samples is minimized;

determining whether said concentration of SOD-1 in the body fluid specimen of the mother is above the threshold minimum concentration, which is indicative of a likelihood of fetal Trisomy 21 Down's syndrome.

2. The method of claim 1 wherein the extra-cellular body fluid is amniotic fluid, plasma, or serum.

3. The method of claim 1 wherein an SOD-1 concentration of substantially 314 ng/ml or greater in an amniotic fluid specimen from a mother in the fifteenth to sixteenth week of pregnancy indicates the presence of Trisomy 21 Down's Syndrome in the fetus.

4. The method of claim 1 wherein the concentrations of SOD-1 are assayed with an assay which is homogeneous or heterogeneous, one or two site immunoassay, using polyclonal or monoclonal antibodies, carried out in solid or liquid phase.

* * * * *